United States Patent [19]
Schoelling

[11] Patent Number: 5,453,085
[45] Date of Patent: Sep. 26, 1995

[54] TAMPON APPLICATOR

[75] Inventor: Hans-Werner Schoelling, Ennepetal, Germany

[73] Assignee: McNeil-PPC, Inc., Milltown, N.J.

[21] Appl. No.: 137,391

[22] Filed: Oct. 14, 1993

Related U.S. Application Data

[63] Continuation of Ser. No. 775,323, Oct. 11, 1991, abandoned.

[30] Foreign Application Priority Data

Oct. 18, 1990 [DE] Germany ............................ 9014464 U

[51] Int. Cl.[6] ..................................................... A61F 13/20
[52] U.S. Cl. ........................................... 604/15; 64/11
[58] Field of Search ................... 604/11–18, 904

[56] References Cited

U.S. PATENT DOCUMENTS

| 3,015,332 | 1/1962 | Brecht | 604/15 |
|---|---|---|---|
| 3,124,134 | 3/1964 | Gardner | 604/15 |
| 3,347,234 | 10/1967 | Voss | 604/14 |
| 3,643,661 | 2/1972 | Crockford | 604/15 |
| 3,696,812 | 10/1972 | Jaycox | 604/18 |
| 3,760,808 | 9/1973 | Bleuer | 128/263 |
| 3,835,856 | 9/1974 | Warncke | 604/15 |
| 4,291,696 | 9/1981 | Ring | 604/14 |
| 4,411,647 | 10/1983 | Sakurai et al. | 604/18 X |
| 4,447,222 | 5/1984 | Sartinoranont | 604/15 |
| 4,479,791 | 10/1984 | Sprague | 604/18 X |
| 4,536,178 | 8/1985 | Lichstein et al. | 604/15 |
| 4,676,773 | 6/1987 | Sheldon | 604/14 X |
| 4,857,044 | 8/1989 | Lennon | 604/904 X |
| 4,921,474 | 5/1990 | Suzuki et al. | 604/16 |
| 4,960,417 | 10/1990 | Tarr, Jr. et al. | 604/15 |

FOREIGN PATENT DOCUMENTS

| 0291343 | 8/1988 | European Pat. Off. . | |
| 0557211 | 5/1958 | Italy | 604/15 |
| 82/02489 | 8/1982 | WIPO . | |
| 90/11747 | 10/1990 | WIPO . | |

Primary Examiner—Jerome L. Kruter
Assistant Examiner—K. M. Reichle

[57] ABSTRACT

The invention is related to a tampon applicator (10) made of plastic, especially for feminine hygiene, consisting of an approximately cylindrical outer sleeve (12) which is intended for receiving a tampon (14) and in the rear end of which there is inserted in an axially non-displaceable manner hollow grip piece (16), in which a slide (18) is arranged so as to be axially movable. The outer face of the slide (18) is connected in the vicinity of its fromt end, to the inner wall of the grip piece (16) by means of at least one predetermined breaking point (24). Thus, the tampon applicator can be produced from just two injection-molded parts allowing reduced expenditure on machinery and assembly. The slide is held captively in the grip piece until the tampon applicator is put to use.

5 Claims, 1 Drawing Sheet

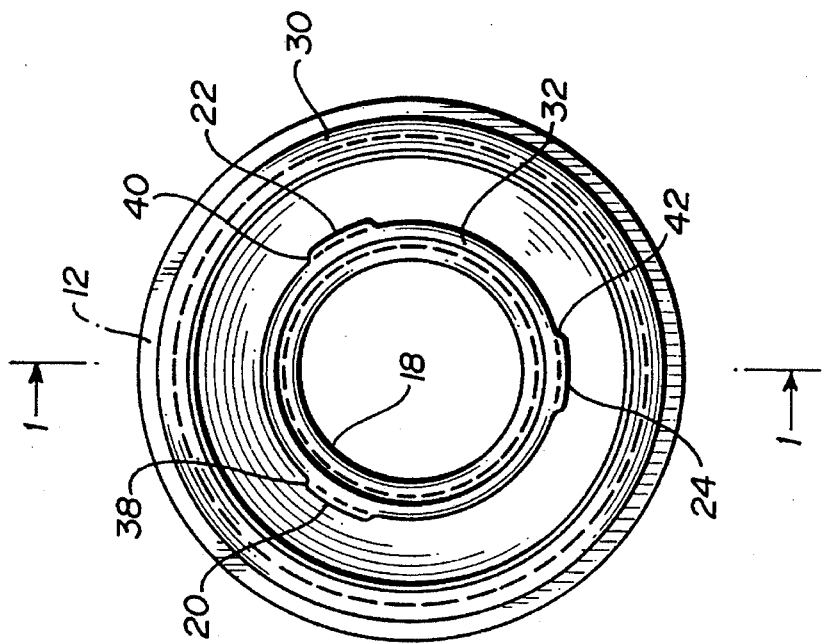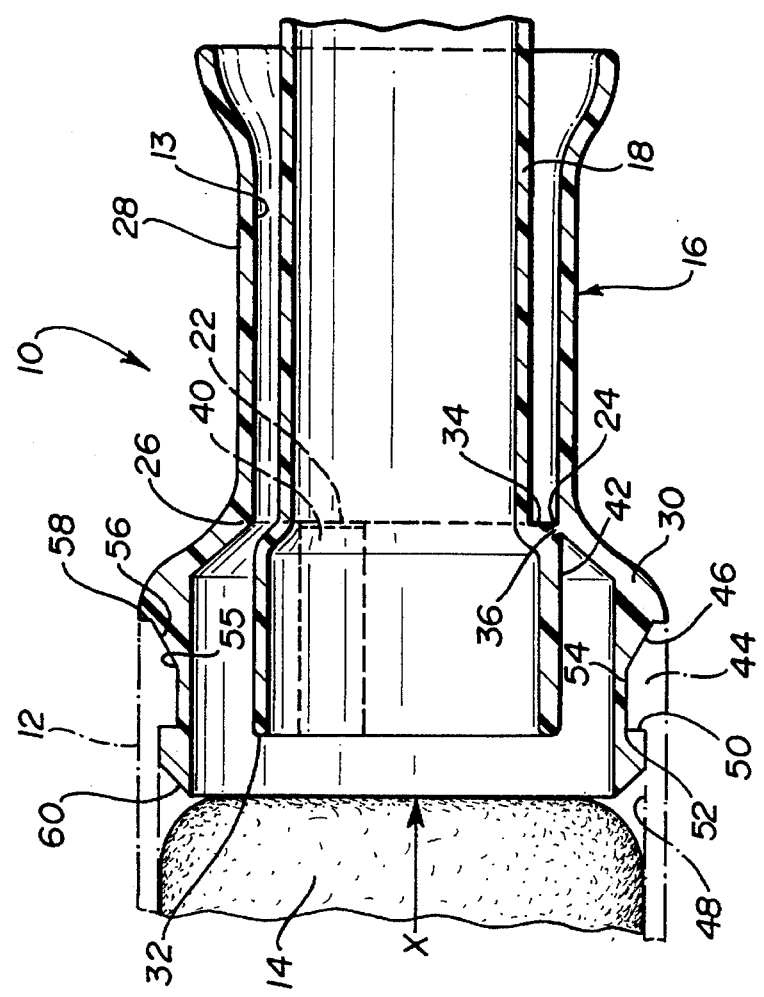

TAMPON APPLICATOR

This is a continuation of application Ser. No. 07/775,323, filed Oct. 11, 1991, now abandoned.

The invention relates to a tampon applicator made of plastic, especially for feminine hygiene, consisting of an approximately cylindrical outer sleeve which is intended for receiving a tampon and in the rear end of which there is inserted in an axially non-displaceable manner a hollow grip piece, in which a slide is arranged so as to be axially movable.

As a rule, the outer sleeve, the grip piece and the slide of tampon applicators of this known type are produced separately by an injection-moulding process and subsequently assembled after insertion of the tampon into the outer sleeve, by inserting the slide into the grip piece and subsequently fitting the grip piece onto the rear end of the outer sleeve. This type of production is, of course, relatively time-consuming and expensive.

SUMMARY OF THE INVENTION

The object on which the invention is based is therefore to improve a tampon applicator of the above-mentioned known type in such a way that its production and assembly can be accomplished with less expenditure in terms of machinery and time.

The invention achieves this object by the outer face of the slide being connected, in the vicinity of its front end, to the inner wall of the grip piece by means of at least one predetermined breaking point.

This makes it possible to produce the tampon applicator from just two injection-moulded parts, allowing the expenditure on machinery and assembly to be reduced considerably. At the same time, it is ensured that the slide is held captively in the grip piece by the at least one predetermined breaking point until the tampon applicator is put to use.

The invention is developed further by the features in the subclaims.

BRIEF DESCRIPTION OF THE DRAWING

FIG. 1 is a view of a longitudinal section along line 1—1 of FIG. 2 showing the tampon applicator with the grip piece connected to the slide by predetermined breaking points, and FIG. 2 is an end elevation viewed in the direction of the arrow "X" in FIG. 1.

DETAILED DESCRIPTION OF THE DRAWING

In the figures, a tampon applicator 10 for feminine hygiene is shown, which consists of an approximately cylindrical outer sleeve 12, a tampon 14 inserted therein, a grip piece 16 and a slide 18. The outer sleeve 12, the grip piece 16 and the slide 18 consist of plastic such as polyethylene, polypropylene or, preferably, a biodegradable plastic, such as mixtures of polyhydroxyvaleric acid or polyhydroxybutyric acid, or of a substance dissolving in connection with water, such as for example polyvinyl alcohol.

The hollow grip piece 16 is inserted in an axially non-displaceable manner into the rear end of the outer sleeve 12 and receives the slide 18 in an axially movable manner. The outer face of the slide 18 is connected, in the vicinity of its front end 32, to the inner wall 13 of the grip piece 16 by means of three predetermined breaking points 20, 22, 24. The predetermined breaking points 20, 22, 24 consist in each case of a thin plastic skin. By connecting the grip piece 16 to the slide 18, a one-part moulding is created, so that the outer sleeve 12 on the one hand and the one-part moulding comprising the grip piece 16 and the slide 18 on the other hand can be injection-moulded in just two moulds.

FIGS. 1 and 2 shows that the three predetermined breaking points 20, 22, 24 are arranged between the slide 18 and the front end 26 of a guide shank 28, of reduced diameter, of the grip piece 16 for the slide 18. The guide shank 28 merges towards the front end of the grip piece 16 into a coupling end 30, of which the inside and outside diameters are widened in relation to the guide shank 28 of the grip piece 16.

The front end 32 of the slide 18 is likewise widened essentially cylindrically in relation to the rear portion of its length to form an outer annular shoulder 34. The outer edge 36 of the annular shoulder 34 is connected to the front end 26 of the guide shank 28 of the grip piece 16 by means of the three predetermined breaking points 20, 22, 24, which are spaced at equal circumferential angles from one another. The annular shoulder 34 of the slide 18 is widened in the region of these predetermined breaking points 20, 22, 24 by means of three outer longitudinal ribs 38, 40, 42 located at the front end 32 of the slide 18, in such a way that, during injection moulding, the outer edge 36 of the annular shoulder 34 permits channeling of the injected material to the grip piece 16 via the predetermined breaking points only in the region of these longitudinal ribs 38, 40, 42.

The rear end of the outer sleeve 12 partially engages over the coupling end 30 of the grip piece 16 and, by means of an inner annular bead 44 engages with a catch fit into an annular groove 46 on the outer face of the said coupling end 30, the profile of the annular groove 46 corresponding to that of the annular bead 44. The profile of the inner annular bead 44 of the outer sleeve 12 is formed by a front annular internal shoulder 50. From the inner edge 52 of this internal shoulder 50 there extends a cylindrical portion 54. This cylindrical portion ends at about half the width of the bead profile with a radial relief 55 of smaller radial width. This relief 55 merges into a conical surface 56. The conical surface 56 widens to a diameter at the rear end face 58 of the outer sleeve 12 which is dimensioned larger than the diameter exhibited by the inner wall 48 of the outer sleeve 12 and, in the assembled state of the tampon applicator 10, by the outer face, bearing against the inner wall 48 in front of the annular bead 44, of the front coupling end 30 of the grip piece 16, engaging over the annular bead. As can be seen, the outside diameter of the coupling end 30 corresponds to the outside diameter of the outer sleeve 12, while the outside diameter of the front part, lying in front of the annular bead, of the coupling end 30 is adapted to the diameter of the inner wall 48 of the outer sleeve 12. The front end face 60 of the coupling end 30 is tapered conically forwards, in order to facilitate the insertion of the coupling end 30 into the rear end of the outer sleeve 12.

As a departure from the preferred exemplary embodiment described above, if appropriate there may also be provided more than three predetermined breaking points, or else just a single predetermined breaking point, extending over the entire circumference of the annular shoulder of the slide, which point is connected to the inner wall of the grip piece in the form of a thin plastic skin. The catch connection between the front coupling end and the outer sleeve permits a simple assembly by insertion of the coupling end into the rear end of the outer sleeve, the predetermined breaking connection between the slide and the grip piece at the same time being broken, so that the slide is mounted by the widened front end captively in the coupling end of the grip piece, but axially displaceably in the latter in the discharge direction of the tampon. Furthermore, it goes without saying that, if appropriate, the slide may also have a different form, as long as it is ensured that, once the predetermined breaking connection with the grip piece has been destroyed, it cannot fall out of the latter to the rear.

I claim:

1. A tampon applicator made of plastic, especially for feminine hygiene, comprising:
   (a) a substantially cylindrical outer sleeve having a longitudinal axis for receiving a tampon;
   (b) a hollow grip piece having a front end, inserted in an axially non-displaceable manner proximate a rear end of the outer sleeve; and
   (c) a slide having a front end connected to an inner wall of the grip piece by means of at least one predetermined breaking point;
wherein the slide is arranged so as to be axially movable within the grip piece and the front end of the slide can contact the tampon held within the outer sleeve.

2. Tampon applicator according to claim 1, wherein the grip piece comprises a guide shank for the slide which merges towards the front end of the grip piece into a coupling end, the coupling end has inside and outside diameters which are larger than an outside diameter of the guide shank, and the at least one predetermined breaking point is arranged between the slide and a front end of the guide shank.

3. Tampon applicator according to claim 2, wherein the front end of the slide is widened to form an outer annular shoulder, having an outer edge which is connected to the front end of the guide shank of the grip piece by means of a plurality of predetermined breaking points, which are spaced at equal arcs about the outer edge.

4. Tampon applicator according to claim 3, wherein the outer annular shoulder of the slide is widened proximate the predetermined breaking points by means of a plurality of outer longitudinal ribs located at the front end of the slide.

5. Tampon applicator according to claim 4, wherein the outer sleeve has an inner wall and an outer wall, and the rear end of the outer sleeve partially engages over an outer face of the coupling end of the grip piece by means of an inner annular bead having a profile that engages with a catch fit into an annular groove on the outer face of said coupling end, wherein the annular groove has a profile corresponding to that of the annular bead.

* * * * *